United States Patent
Holthaus et al.

(10) Patent No.: US 6,443,968 B1
(45) Date of Patent: *Sep. 3, 2002

(54) DUAL CAM TRIGGER FOR A SURGICAL INSTRUMENT

(75) Inventors: Mark L. Holthaus, Batavia; Mark S. Zeiner, Milford, both of OH (US)

(73) Assignee: Ethicon Endo-Surgery, Inc., Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/562,250

(22) Filed: May 2, 2000

Related U.S. Application Data

(63) Continuation of application No. 09/353,482, filed on Jul. 13, 1999, now abandoned, which is a continuation of application No. 08/947,690, filed on Oct. 9, 1997, now Pat. No. 5,954,746.

(51) Int. Cl.[7] ................................................. A61B 17/28
(52) U.S. Cl. ........................ 606/169; 606/205; 606/170; 606/174; 606/208
(58) Field of Search ................................. 606/205, 206, 606/208, 170, 174, 169, 148, 147, 51, 52

(56) References Cited

U.S. PATENT DOCUMENTS

| | | |
|---|---|---|
| 388,607 A | 8/1888 | Whitehall |
| 984,756 A | 2/1911 | Frisch |
| 1,009,009 A | 11/1911 | Banchand et al. |
| 1,561,681 A | 11/1925 | Barnes |
| 1,887,376 A | 9/1932 | Wright et al. |
| 2,496,309 A | 2/1950 | Pugh .............................. 81/84 |
| 2,506,831 A | 5/1950 | Hawkins et al. ............. 128/319 |
| 2,600,512 A | 6/1952 | Mead ............................. 81/44 |
| 2,724,300 A | 11/1955 | Ohman .......................... 81/83 |
| 2,842,996 A | 7/1958 | Coslow et al. ................ 81/378 |
| 2,854,877 A | 10/1958 | Hunt .......................... 81/383.5 |
| 3,142,212 A | 7/1964 | Grape ........................ 81/383.5 |
| 4,484,441 A | 11/1984 | Kobayashi et al. ............ 60/285 |
| 4,573,622 A | 3/1986 | Green et al. ................... 227/19 |
| 4,733,671 A | 3/1988 | Mehl .......................... 128/754 |
| 4,869,414 A | 9/1989 | Green et al. ................... 227/19 |
| 4,907,591 A | 3/1990 | Vasconcellos et al. ....... 606/154 |
| 5,184,625 A | 2/1993 | Cottone, Jr. et al. ......... 128/751 |
| 5,251,441 A | 10/1993 | Cottone, Jr. et al. ......... 128/751 |
| 5,251,638 A | 10/1993 | Cottone, Jr. et al. ......... 128/751 |
| 5,322,055 A | 6/1994 | Davison et al. ................ 601/2 |
| 5,337,937 A | 8/1994 | Remiszewski et al. ...... 227/182 |
| 5,465,895 A | 11/1995 | Knodel et al. ............... 227/176 |
| 5,487,500 A | 1/1996 | Knodel et al. ............. 227/181.1 |
| 5,553,765 A | 9/1996 | Knodel et al. ............ 227/176.1 |

(List continued on next page.)

FOREIGN PATENT DOCUMENTS

| | | |
|---|---|---|
| JP | 63-61609 | 3/1988 |
| JP | 8-275952 | 10/1996 |
| JP | 9-38099 | 2/1997 |
| JP | 9-38100 | 2/1997 |
| JP | 9-131350 | 5/1997 |
| RU | 728848 | 5/1980 |

Primary Examiner—Michael H. Thaler

(57) ABSTRACT

The present invention is directed to a surgical instrument such as, for example, an ultrasonic surgical cutting and coagulating device, wherein the gripping movement of the surgeon is mechanically translated into lateral movement for actuating, for example, an actuating rod. One embodiment of the present invention includes a camming pivot for use in surgical instruments, wherein the camming pivot comprises an actuation mechanism, including; a lever arm; a first cam at a distal end of the lever arm; and a second cam positioned distally from the first cam.

15 Claims, 10 Drawing Sheets

U.S. PATENT DOCUMENTS

| | | | |
|---|---|---|---|
| 5,562,241 A | 10/1996 | Knodel et al. | 227/175.1 |
| 5,597,107 A | 1/1997 | Knodel et al. | 225/175.2 |
| 5,637,111 A | 6/1997 | Sutcu et al. | 606/51 |
| 5,653,721 A | 8/1997 | Knodel et al. | 606/151 |
| 5,662,258 A | 9/1997 | Knodel et al. | 227/175.1 |
| 5,662,667 A | 9/1997 | Knodel et al. | 606/151 |

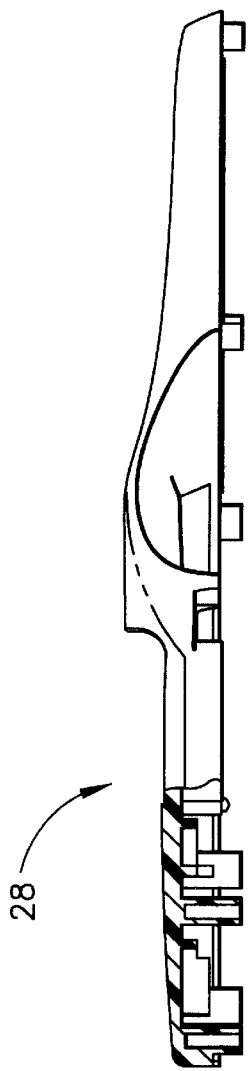
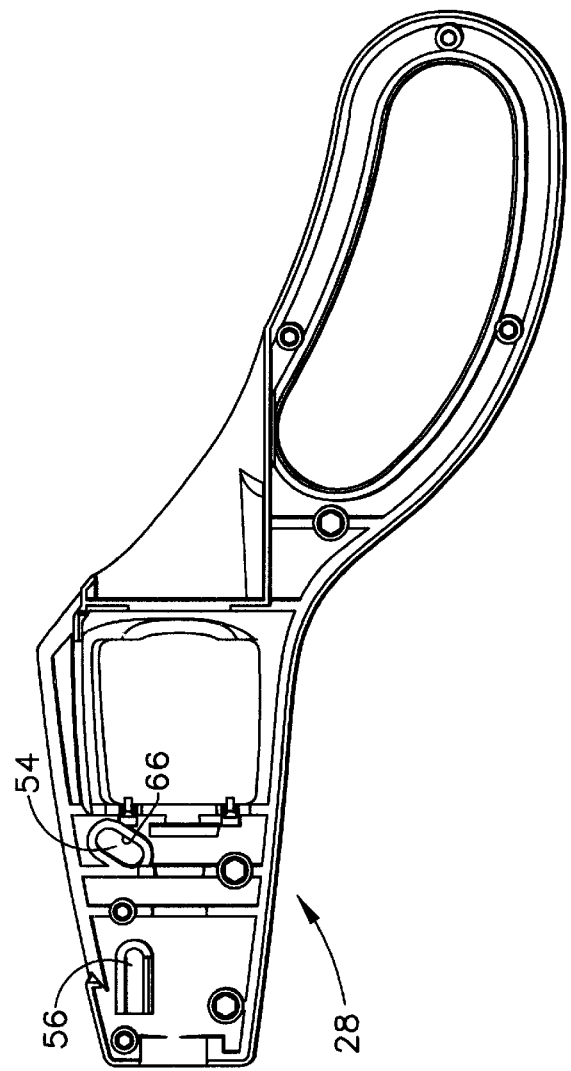
FIG. 4
FIG. 5

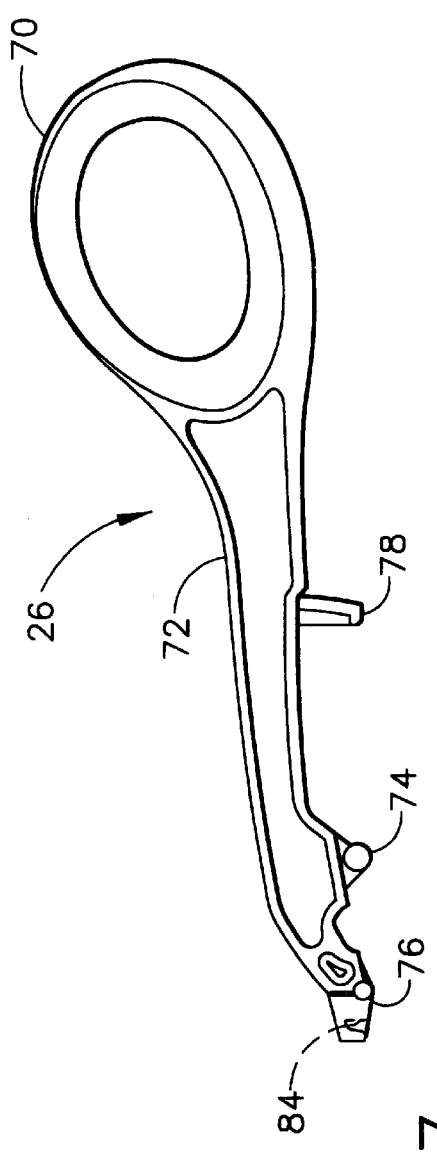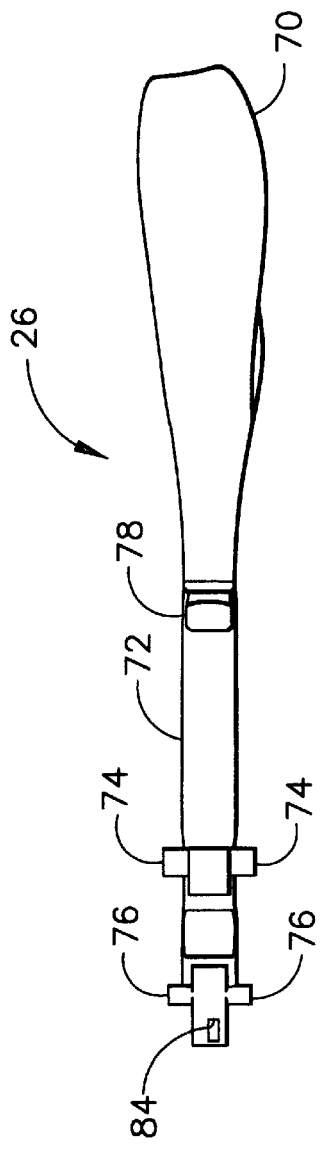
FIG. 7
FIG. 8

DUAL CAM TRIGGER FOR A SURGICAL INSTRUMENT

This application is a continuation of Ser. No. 09/353,482 filed Jul. 13, 1999 now abandoned, which is a continuation of Ser. No. 08/947,690 filed Oct. 9, 1997 now U.S. Pat. No. 5,954,746.

FIELD OF THE INVENTION

The present invention relates, in general, to an improved handle for surgical instruments and, more particularly, to an improved scissor type handle wherein the movable handle element is attached to the body of the instrument by a camming mechanisim including a first cam and a second cam.

BACKGROUND OF THE INVENTION

U.S. Pat. No. 322,055 describes an ultrasonic surgical apparatus which includes a surgical instrument having a handpiece with a transducer for converting an electrical signal into longitudinal vibratory motion. The longitudinal vibratory motion is transmitted to an ultrasonic blade which is connected to the handpiece. An accessory is releasably connected to the handpiece to enable clamping of tissue against the vibrating blade to afford improved coagulating and cutting of tissue. In U.S. Pat. No. 5,322,055 Scissors-like grips actuate a pivoted clamp jaw along one side of the ultrasonically vibrating blade to compress and bias tissue against the blade in a direction which is substantially normal to the direction of longitudinal vibratory movement. In U.S. Pat. No. 5,322,055, the clamp jaw and blade are rotatable relative to one another to align a selected blade edge of a multi-edged blade with the clamp jaw for cutting and coagulating while clamping or circumferentially spacing a selected blade edge from the clamp jaw for cutting and coagulating without clamping. U.S. Pat. No. 5,322,055 is hereby incorporated herein by reference.

Many surgical instruments, such as the ultrasonic surgical device illustrated and descried in U.S. Pat. No. 5,322,055, use elements such as actuation rods to transmit force from the proximal end of the instrument, where the instrument is gripped by the surgeon, to the distal end of the instrument where the transmitted force is used to actuate an end effector such as, for example, a clamping jaw. In order to effectively transmit force from the surgeons hand to the end effector in such an instrument, it is necessary to translate the grasping motion of the surgeons fingers to the lateral motion of the actuation rod. Scissors type grips are used in many surgical devices of this kind because they are comfortable and tend to be familiar to the surgeon. Many such instruments use a single pivot pin in combination with a cam of some type to translate the arcuate motion of the scissor grip to the linear motion of the actuation rod. However, in certain circumstances, such an arrangement may not be acceptable, such as, for example, where the room in the instrument body is limited and rotational movement of the grip around a fixed pivot pin requires too much of the available room. Further, in order to increase the stroke in pivot pin arrangement, it is generally necessary to increase the distance from the pivot pin to the cam, requiring more room if a longer stroke is desired. It would, therefore, be advantageous to provide an improved actuation mechanism for translating the grasping motion of a human hand to the lateral motion necessary to drive an actuation rod. In particular, it would be advantageous to provide such an improved actuation mechanism without using a fixed pivot pin type arrangement. It would also be advantageous to provide such an improved actuation mechanism in an in line handle arrangement and to reduce the room necessary for the actuation mechanism without substantially reducing the stroke length of the actuation rod.

SUMMARY OF THE INVENTION

The present invention is directed to a surgical instrument such as, for example, an ultrasonic surgical cutting and coagulating device, wherein the gripping movement of the surgeon is mechanically translated into lateral movement to move, for example, an actuating rod. One embodiment of the present invention includes a camming pivot for use in surgical instruments, wherein the camming pivot includes: a lever arm; a first cam at a distal end of the lever arm; and a second cam positioned distally from the first cam. In one embodiment of the present invention, the first and second cams may comprise, for example, camming pivot pins moveable within first and second camming slots. In a further embodiment of the invention, the first camming slot may include a curved or angular interior camming surface.

In a further embodiment of the present invention, a surgical device includes an end effector, a camming pivot actuation mechanism and an actuation rod connecting the end effector to the actuation mechanism. In such an instrument, the actuation rod is gennerally positioned substantially parallel to the central axis of the instrument. The end effector may include, for example, an ultrasonic blade and a movable clamping element disposed opposite the ultrasonic blade. The actuation mechanism, which is operatively connected to the moveable clamping element by, for example, the actuation rod, may include a lever arm and first and second cams at a distal end of the lever arm. In this embodiment of the invention, the first cam may comprise, for example, a first camming pin positioned on the lever arm and a first camming slot operatively associated with the first camming pin where in the first camming slot is positioned at an angle to the central axis of the instrument. The second cam may comprise, for example, a second camming pin positioned on the lever arm distally from the first cam and a second camming slot operatively associated with the second camming pin, with the second camming slot being positioned substantially parallel to the central axis of the instrument.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 4 is a plan view of the right hand portion of the housing of the clamp coagulator accessory partially broken away for clarity.

FIG. 5 is a centerline side elevation view of the right hand housing of the clamp coagulator accessory.

FIG. 7 is a side elevation view of the clamp jaw actuation mechanism of the clamp coagulator accessory.

FIG. 8 is a bottom plan view of the clamp jaw actuation mechanism of the clamp coagulator accessory.

DETAILED DESCRIPTION OF THE INVENTION

Figure 1:
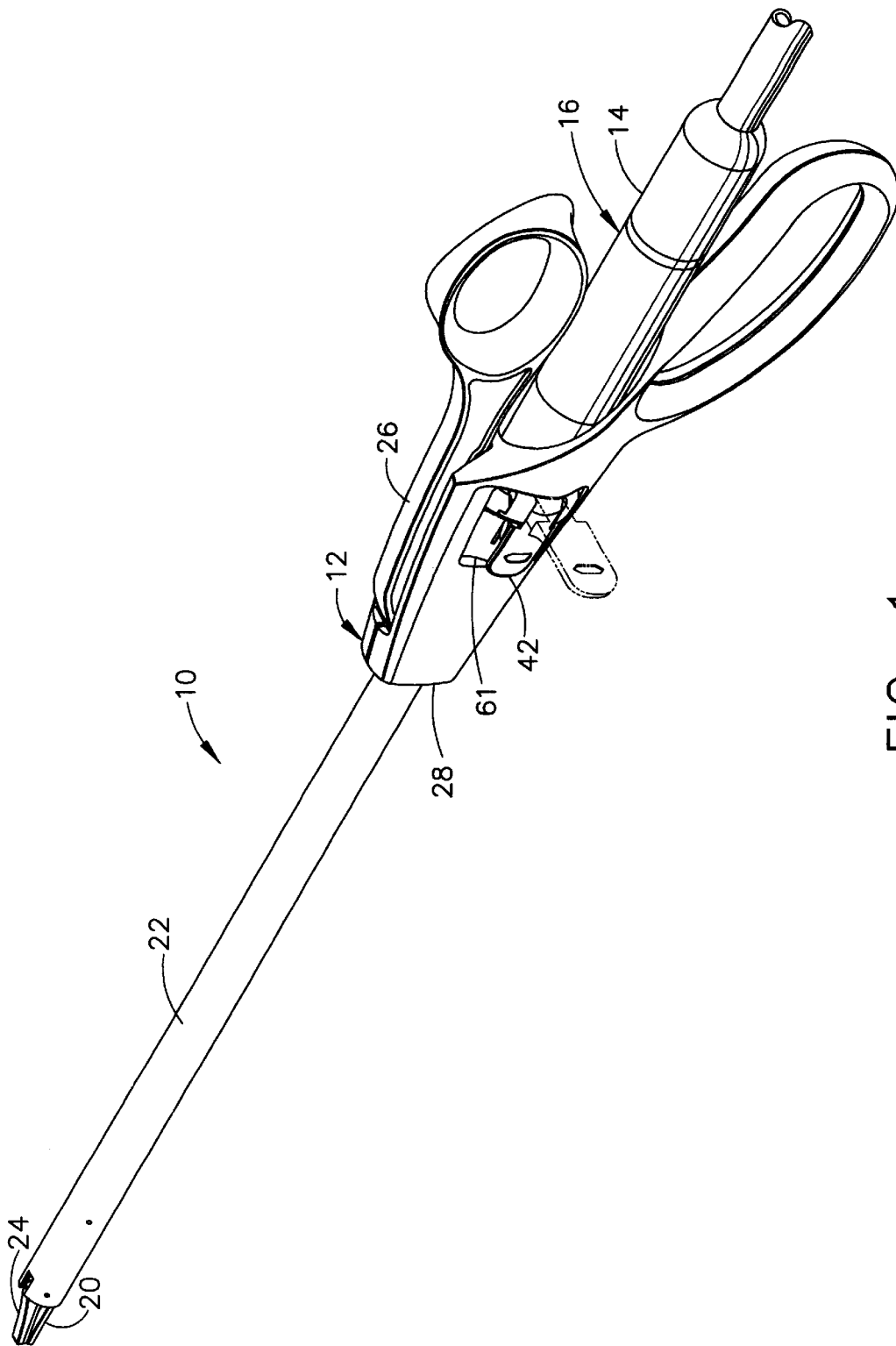
FIG. 1 is an isometric view of an ultrasonic surgical device constructed in accordance with a preferred embodiment of the present invention.
Figure 1A:
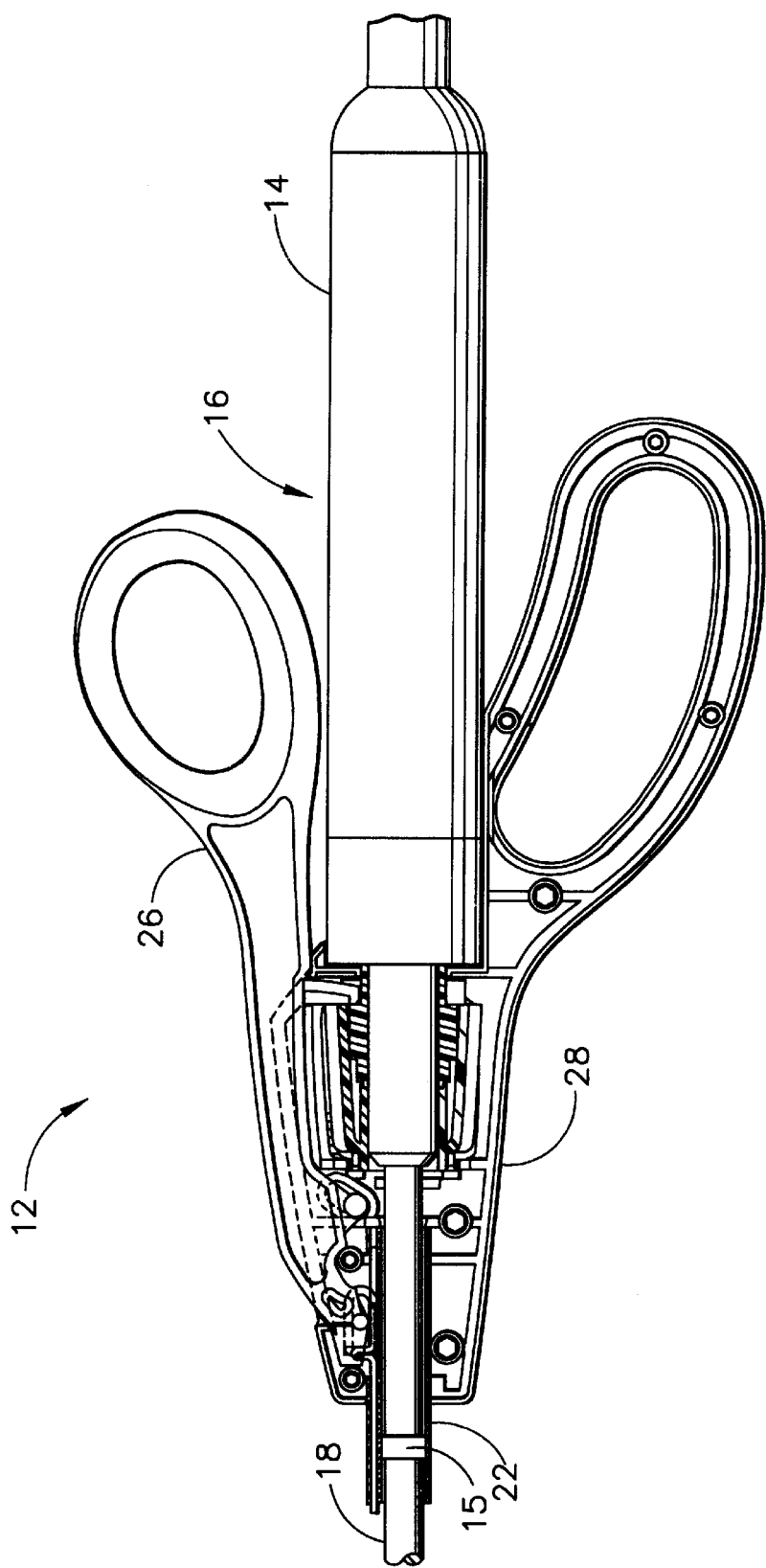
FIG. 1A is a centerline section view of the handle portion of the instrument of FIG. 1.

FIG. 1 is an isometric view of an ultrasonic surgical device constructed in accordance with a preferred embodiment of the present invention. FIG. 1A is a centerline section view of the handle portion of the instrument of FIG. 1. In FIGS. 1 and 1A ultrasonic surgical device 10 includes an ultrasonic surgical instrument 16 and a clamp coagulator accessory 12. Ultrasonic instrument 16 comprises a housing or handpiece 14 in combination with an ultrasonic blade 20 and, in some embodiments, a blade coupler extension which connects handpiece 14 to blade 20. Handpiece 14 houses a transducer (not shown), preferably a piezeoceramic transducer, for converting an electrical signal, for example, a 55,000 Hz sinusoidal waveform, into a mechanical longitudinal vibration. As described in detail in U.S. Pat. No. 5,322,055, which was previously incorporated herein by reference, surgical instrument 10 includes a blade coupler extension 18 which extends from housing 14 through elongated tube 22 and carries ultrasonic blade 20. Thus, ultrasonic vibrations are transmitted from the transducer in handpiece 14, longitudinally along the blade coupler extension 18 to blade 20. In FIGS. 1 and 1A, elongated tube 22 surrounds the blade coupler extension 18.

Figure 2:
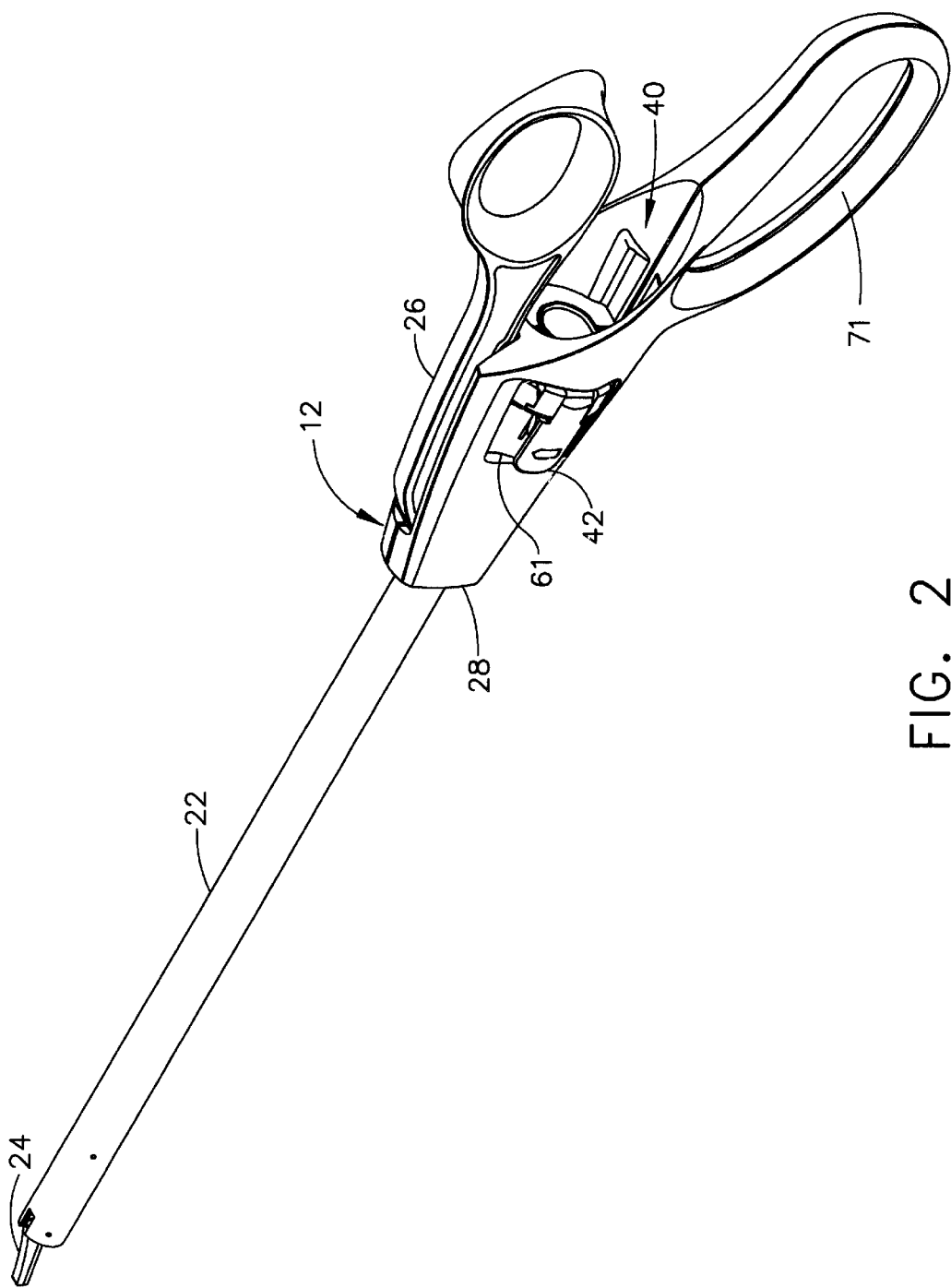
FIG. 2 is an isometric view of a clamp coagulator accessory according to the present invention.

FIG. 2 is an isometric view of a clamp coagulator accessory according to the present invention. In FIG. 2, clamp coagulator accessory 12 includes an elongated tube 22 pivotally carrying a clamping jaw 24 at its distal end and a clamp jaw actuation mechanism 26 at its proximal end. Accessory 12 also includes accessory housing 28 which supports clamp jaw actuation mechanism 26 and elongated tube 22. Accessory housing 24 further supports rotation control knob 61 which includes mounting lever 42. Accessory housing 28 further includes a generally cylindrical fitting having a proximal axial bore 40 for receiving the distal end of handpiece 14. In the embodiment of the invention illustrated and described herein, finger ring 71 is affixed to and suported by accessory housing 28.

Figure 3:
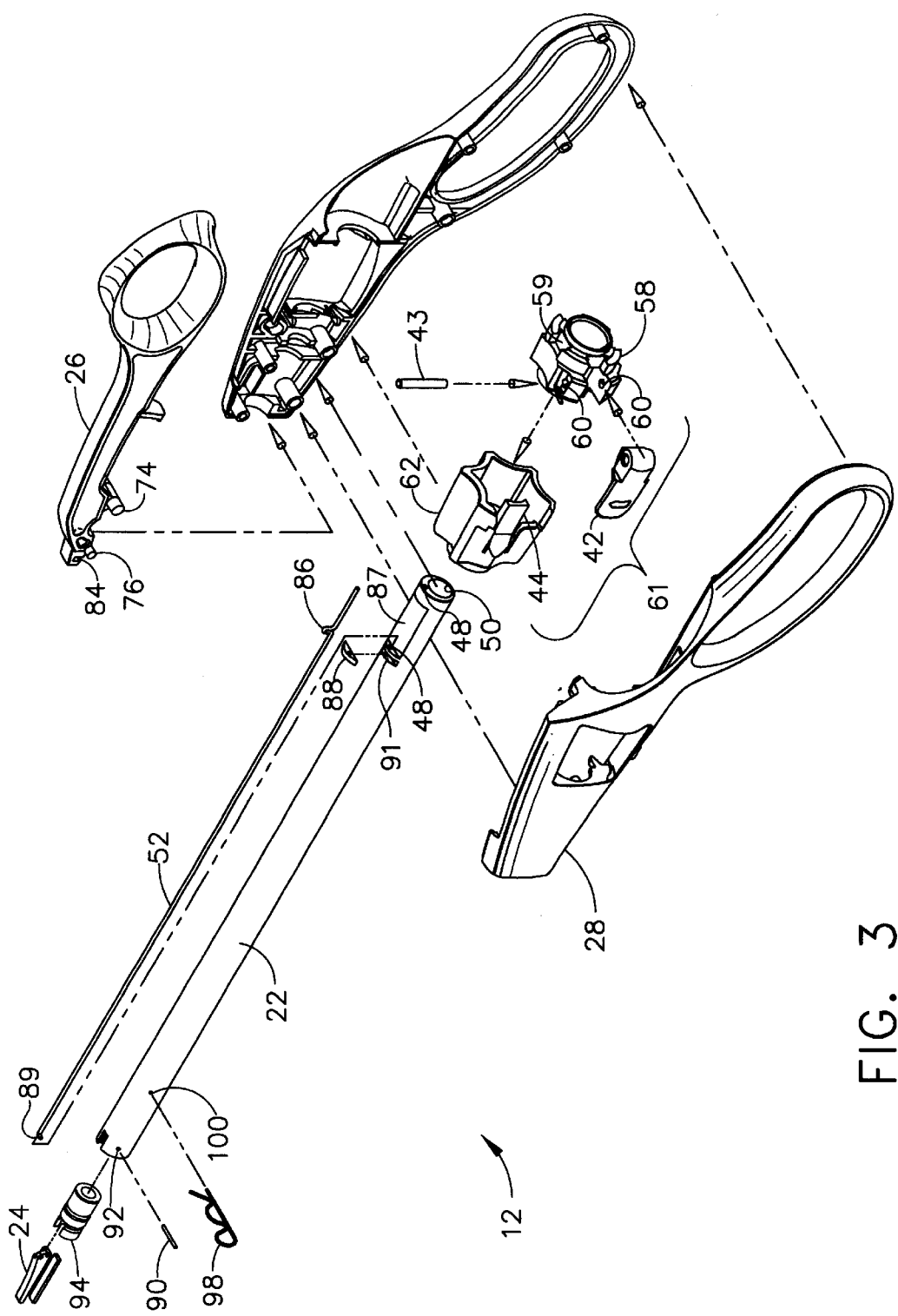
FIG. 3 is an exploded isometric view of the clamp coagulator accessory illustrated in FIG. 2.

FIG. 3 is an exploded isometric view of the clamp coagulator accessory illustrated in FIG. 2. As illustrated in FIG. 3, elongated tube 22 has a first axial bore 48 and a second axial bore 50. First axial bore 48 carries an actuating rod 52 for actuating clamp jaw 24. When clamp coagulator accessory 12 is mounted to ultrasonic surgical instrument 16 as illustrated in FIG. 1, second axial bore 50 receives ultrasonic blade 20, which is mounted on blade coupler extension 18. Thus, a clamp coagulator accessory such as clamp coagulator accessory 12 may be fitted over an ultrasonic instrument such as ultrasonic surgical instrument 16 to form ultrasonic surgical device 10. Mounting lever 42 is pivotally mounted by lever mounting pin 43 to rotation control knob 61, which also includes compression pad 44. Rotation control knob 61 is divided into two parts for ease of manufacture. Lever mounting assembly 58, which includes pivot pin holes 60 and knob positioning slots 59, snaps into thumb wheel 62 to form rotation control knob 61. When clamp coagulator accessory 12 is assembled, tube 22 is suitably fixed to accessory housing 28.

In FIG. 3, actuation rod 52 is slideably positioned in first axial bore 48 with wireform 86 positioned in opening 87. Shim 88, which may be constructed of, for example, silicone, is positioned in slot 91 such that actuation rod 52 passes through shim 88 as it moves in axial bore 48. At its distal end, elongated tube 22 includes support bushing 94 which may be constructed of, for example, Teflon. Clamping jaw 24 is affixed to elongated tube 22 by jaw pivot pin 90 which is positioned in pivot pin guide hole 92. Elongated tube 22 further includes alignment guide hole 100 which is adapted to receive alignment pin 98.

Clamp jaw actuation mechanism 26 is illustrated in FIG. 3 and further illustrated in greater detail in FIGS. 7 and 8. FIG. 7 is a side elevation view of the clamp jaw actuation mechanism of the clamp coagulator accessory. FIG. 8 is a bottom plan view of the clamp jaw actuation mechanism of the clamp coagulator accessory. Clamp jaw actuation mechanism 26 includes thumb ring 70 at its proximal end. Thumb ring 70 is connected to a first camming pin 74 and a second camming pin 76 by lever arm 72. Rotation locking flange 78 extends from the inner surface of lever arm 72. Notch 84, which is designed to receive wire form 86, is positioned at the distal end of lever arm 72.

Figure 6:
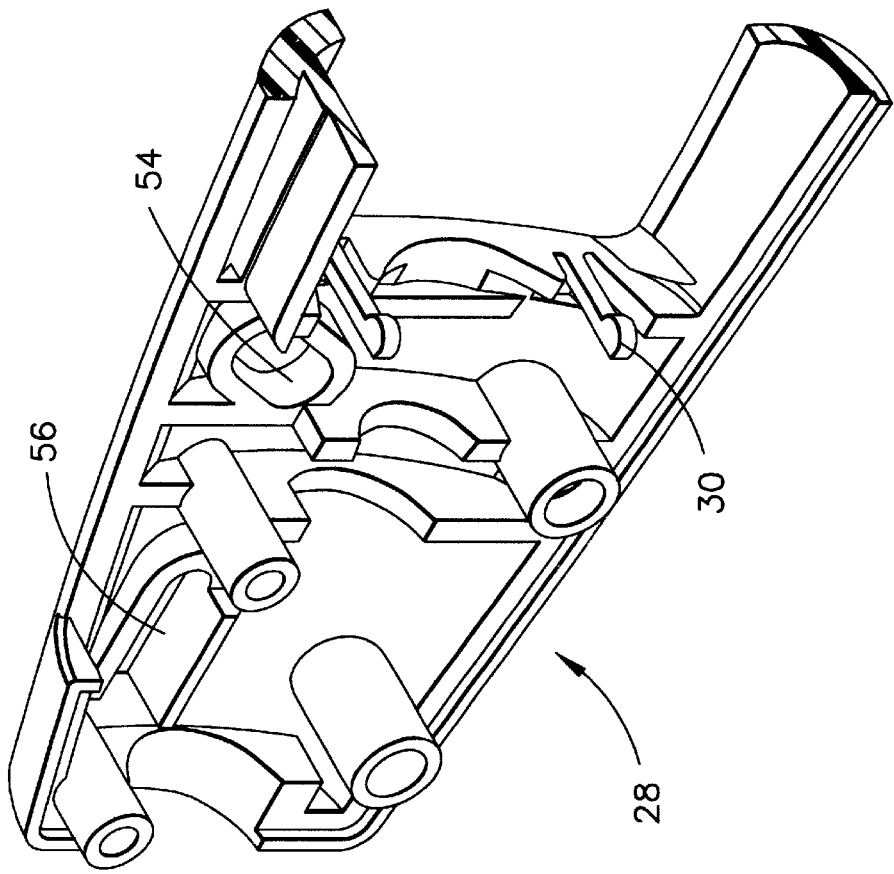
FIG. 6 is an enlarged fragmentary isometric view of the distal portion of the right hand housing of the clamp coagulator accessory.

FIG. 4 is a plan view of the right hand portion of the housing of the clamp coagulator accessory partially broken away for clarity. FIG. 5 is a centerline side elevation view of the right hand housing of the clamp coagulator accessory. FIG. 6 is an enlarged fragmentary isometric view of the distal portion of the right hand housing of the clamp coagulator accessory. As illustrated in FIG. 3 and in greater detail in FIGS. 5 and 6, accessory housing 28 includes detent flanges 30, first camming channel 54 and second camming channel 56. First camming channel 54 and second camming channel 56 are positioned and adapted to receive first camming pin 74 and second camming pin 76 respectively. It will be apparent that, in the embodiment of the invention described and illustrated herein, both halves of accessory housing 28 will prefeably include both first camming channel 54 and second camming channel 56. However, in other embodiments of the present invention, it may be enough to include camming channels on only one half of accessory housing 28 or to include first camming channel 54 on one half of housing 28 and second camming channel 56 on the other half of housing 28.

Figure 11:
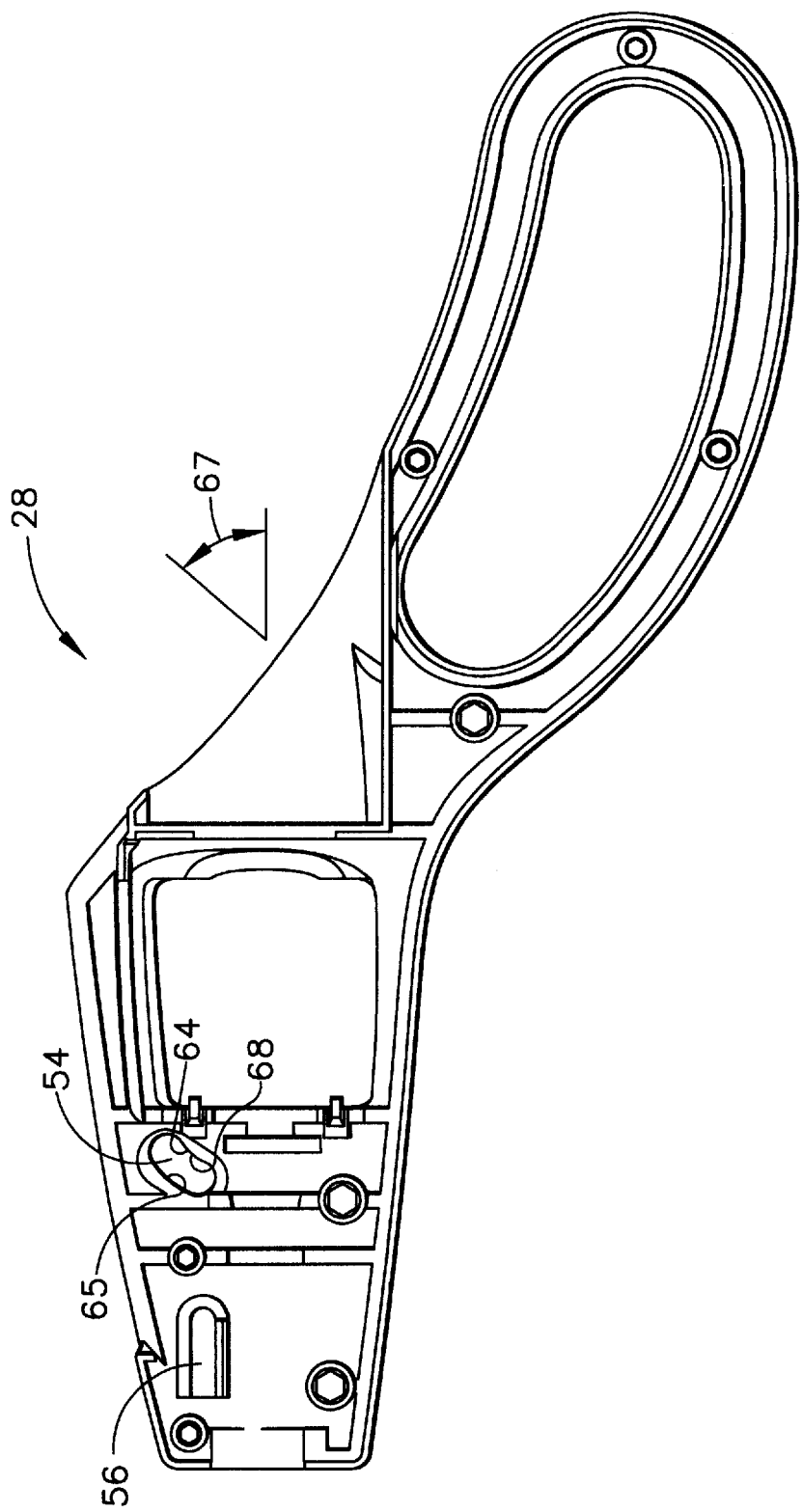
FIG. 11 is a centerline side elevation view of the right hand housing of the clamp coagulator accessory according to a further embodiment of the present invention.

FIG. 11 is a centerline side elevation view of the right hand housing of the clamp coagulator accessory according to a further embodiment of the present invention. In the embodiment of the invention illustrated in FIG. 11, first camming slot 54 includes a first interior camming surface 64 which is substantially convex in shape. In this embodiment, first camming slot 54 further includes a second camming surface 65 which is substantially concave in shape. Thus, in the embodiment of FIG. 11, first camming slot 54 is substantially arcuate in shape.

In operation, it will be appreciated that ultrasonic surgical instrument 16 may be used with or without a blade coupler extension 18 for cutting and coagulating in a conventional manner. Likewise, clamping jaw 24 may be disposed directly on accessory housing 28 depending upon the desired length of the resulting surgical device. Thus, a surgical device 10 according to the present invention may be provided in different lengths for different surgical purposes. For endoscopic, particularly laparoscopic use, extension 18 is applied to the handpiece 14 and the accessory 12 includes elongated tube 22 housing blade coupler extension 18. Thus, in the illustrated form, ultrasonic surgical device 10 and, more particularly, clamp coagulator accessory 12 are adapted for use in either laparoscopic or open surgery. Blade coupler extension 18 carries a plurality of longitudinally spaced rings 15, preferably formed of silicone, located at the node points of the blade coupler extension 18 to minimize or eliminate dissipation of the ultrasonic longitudinal vibration of the blade coupler extension 18 by contact with the inner surface of second axial bore 50 of tube 22.

Attachment of ultrasonic surgical instrument 16 to clamp coagulator accessory 12 is accomplished using mounting lever 42 which, when closed, compresses clamp pad 44 against the outer surface of housing 14 for frictional engagement along the outer surface of the distal end of handpiece 14. Thus, rotational control knob 61 of accessory 12 and handpiece 14 are frictionally attached one to the other against longitudinal and rotational movement. Mounting lever 42 operates as an over-center toggle and pivots between accessory mounting and demounting positions relative to handpiece 14, as illustrated by the full and dashed lines in FIG. 1.

In order to ensure that ultrasonic blade 20 is properly aligned with clamping jaw 24 when clamping jaw 24 is closed, knob positioning slots 59 on rotation control knob 61 are positioned opposite rotation locking flange 78 when clamp jaw actuation mechanism 26 is opened and closed. Detent flanges 30 on accessory housing 28 are used to assist in aligning knob positioning slots 59 with rotation locking flange 78. Detent flanges 30 extend from accessory hosing 28 and are arranged to engage detents (not shown) in the distal end of rotation control knob 61. Thus, with detent flanges 30 positioned in the appropriate detents in control knob 61, knob positioning slots 59 will be aligned to receive rotation locking flange 78. Further, when rotation locking flange 78 is positioned in one of knob positioning slots 59, rotation control knob and blade 20 are locked in position and cannot be moved relative to accessory housing 28 and clamping jaw 24 respectivly.

Figure 9:
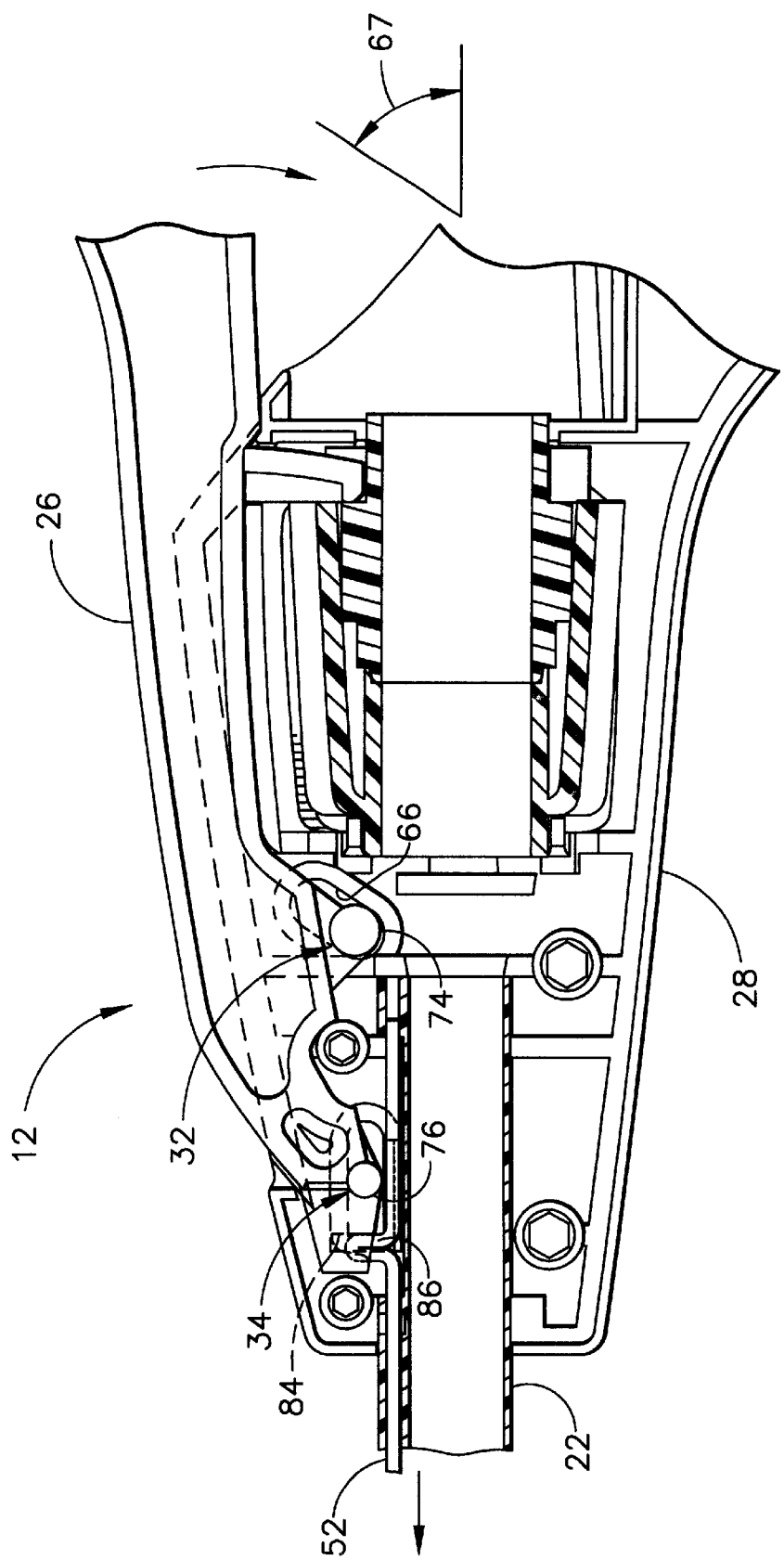
FIG. 9 is an enlarged centerline section view of a portion of the clamp coagulator accessory with the clamp jaw actuation mechanism 26 a closed position.
Figure 10:
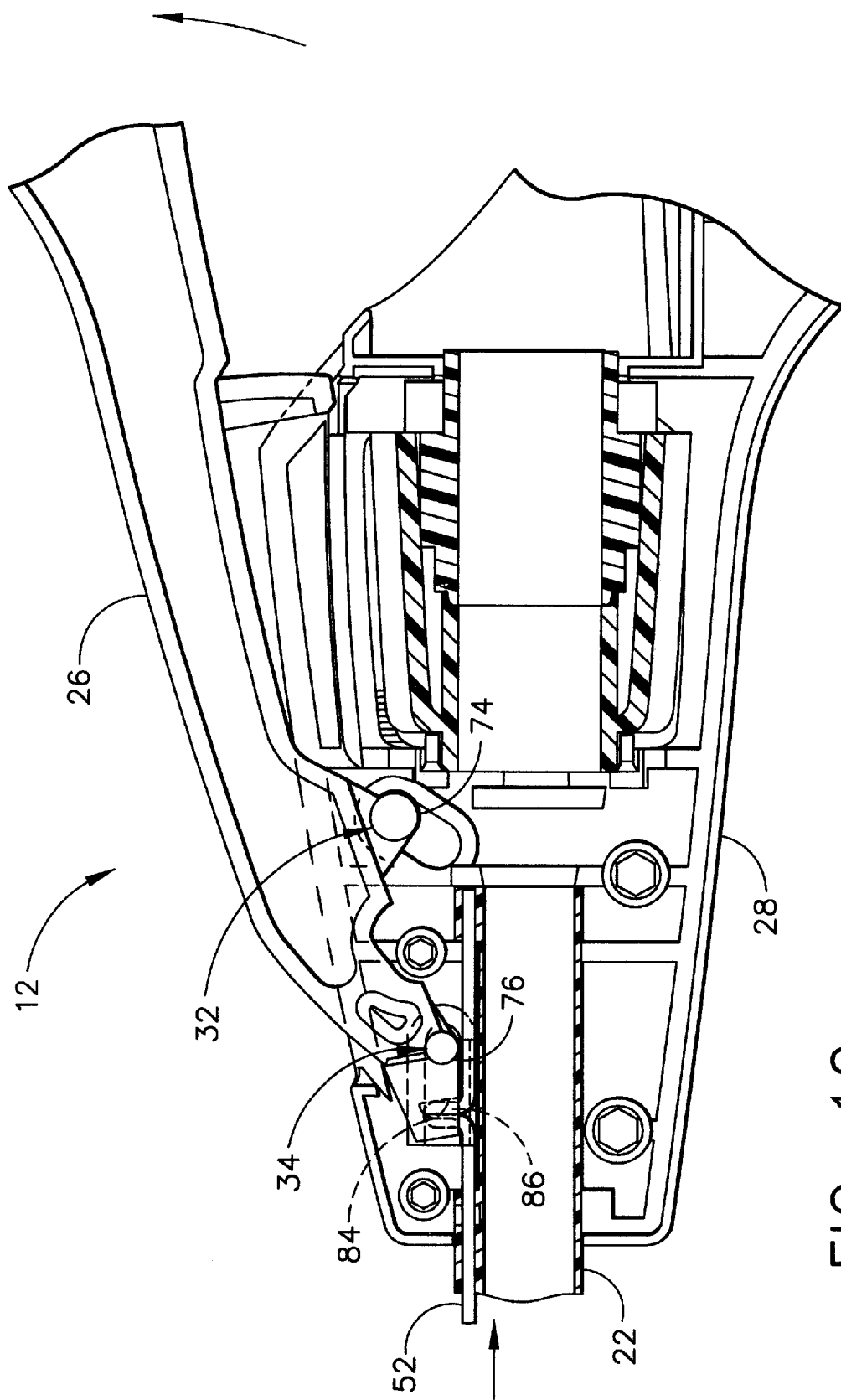
FIG. 10 is an enlarged centerline section view of a portion of the clamp coagulator accessory with the clamp jaw actuation mechanism in an open position.

Operation of the invention may best be understood with reference to FIGS. 1–10 and, in particular, to FIGS. 9 and 10. FIG. 9 is an enlarged centerline section view of a portion of clamp coagulator accessory 12 with clamp jaw actuation mechanism 26 in a first, closed position which corresponds to clamping jaw 24 in its clamped or closed position. FIG. 10 is an enlarged centerline section view of a portion of clamp coagulator accessory 12 with clamp jaw actuation mechanism 26 in a second, open position which corresponds to clamping jaw 24 in its unclamped or open position. In operation, movement of clamp jaw actuation mechanism 26 from its first, closed position (as illustrated in FIG. 9) to its second, open position (as illustrated in FIG. 10) results in movement of clamping jaw 24 from its closed position to its open position. Conversely, movement of clamp jaw actuation mechanism 26 from its second, open position (as illustrated in FIG. 10) to its first, closed position (as illustrated in FIG. 10) results in movement of clamping jaw 24 from its closed position to its open position.

As illustrated in FIG. 9, with clamp jaw actuation mechanism 26 in its first, closed position, camming pins 74 and 76 are at the distal most point of their travel and notch 84 is at the distal most point of its travel. Thus, in FIG. 9, actuation rod 52 has been pushed distally along first axial bore 48 by the interaction of notch 84 and wireform 86. Shim 88 acts to add drag to the movement of actuation rod 52, improving the feel of the device. Actuation rod 52, being connected to clamping jaw 24 by jaw hook 89, pushes on clamping jaw 24, which pivots around jaw pivot pin 90 to its closed position. As illustrated in FIG. 10, with clamp jaw actuation mechanism 26 in its second, open position, camming pins 74 and 76 are at the proximal most point of their travel and notch 84 is at the proximal most point of its travel. Thus, in FIG. 9, actuation rod 52 has been pulled proximally along first axial bore 48 by the interaction of notch 84 and wireform 86. Actuation rod 52, being connected to clamping jaw 24 by jaw hook 89, pulls on clamping jaw 24, which pivots around jaw pivot pin 90 to its open position.

As clamp jaw actuation mechanism 26 moves from its first, closed position to its second, open position, camming pins 74 and 76 move along camming channels 54 and 56 respectively. Thus, the substantially arcuate motion of actuation mechanism 26 is translated into the substantially linear motion of notch 84 which, in turn, moves actuation rod 52 along first axial bore 48. In the embodiment of the invention illustrated in FIGS. 9 and 10, first camming channel 54 and first camming pin 74 comprise first cam 32. Further, in that embodiment, second camming channel 56 and second camming pin 74 comprise second cam 34. First cam 32 and second cam 34 act as a mechanical linkage which transforms the arcuate or rotary motion of actuation mechanism 26 into the substantially linear motion of notch 84. Thus, in, for example, cam 32, first camming pin 74 rotates and slides within first camming slot 54 while, in cam 34, second camming pin 76 rotates and slides within second camming slot 56. Other camming arrangements may be suitable for use in the present invention. For example, it will be apparent that, for the purposes of the present invention, it is not necessary to have camming channels on both halves of housing 28 or to have camming pins on both sides of clamp jaw actuation mechanism 26. A first cam 32 and a second cam 34 positioned on one side of accessory housing 28 or a first cam 32 on a first side of accessory housing 28 and a second cam 34 on a second side of housing 28 would also function in accordance with the present invention. Further, by incorporating one or both of the camming slots into jaw actuation mechanism 26, each cam may comprise a single camming pin extending from one side of housing 28 to the other side, passing through the camming slots in jaw actuation mechanism 26.

In the embodiment of the invention illustrated in FIG. 11, first interior camming surface 64 being substantially convex and second interior camming surface 65 being substantially concave, first camming channel is substantially arcuate in shape. Thus, in the embodiment of FIG. 11, first camming pin 74 will move in an arc as clamp jaw actuation mechanism 26 is opened and closed. By using an arcuate shape for first camming channel 54, the stroke length of actuation rod 52 may be increased more than the corresponding increase in the travel of thumb ring 70 ensuing that clamping jaw 24 may be opened to a desired gap while keeping the travel of thumb ring 70, within a range which is comfortable for the surgeon operator. It will be apparent that the use of various shapes for first camming channel 54 may provide a number of advantages in stroke length and force transmission, depending upon the shape chosen. It will also be apparent that various shapes may be chosen without departing from the scope of the present invention, including, for example, an angular camming channel with a bend between the open and the closed position to change the mechanical advantage (i.e. the percent of force exerted on clamp jaw actuation mechanism 26 which is transmitted to clamping jaw 24) over the range of travel of clamp jaw actuation mechanism 26. For example, it may be advantageous if a smaller percent of the force exerted is applied during the last portion of the closing stroke.

For the purposes of the present invention, the interior angle which is formed at the intersection of the cam tangent line with the central axis of the medical instrument in question may be referred to as the camming angle. The cam tangent line is a line which is parallel to the proximal most elongated wall of the proximal most camming slot or, in the case of a curved or angular slot, which tangential to the distal most point of the proximal most elongated wall of the proximal most camming slot. The central axis of the medical instrument is a line running through the instrument which is substantially parallel to the centerline of the instrument. For the purposes of the present invention, the central axis may be defined as a line which is substantially parallel to the actuation rod. Finally, the interior angle is the proximal most angle at the intersection of the target line with the central axis.

In the clamp jaw actuation mechanism illustrated in FIGS. 1–10 and, more particularly in FIG. 9, the cam tangent line is a line which is parallel to proximal most elongated wall 66 of slot 54. The central axis is a line running parallel to actuating rod 52. The angle 67 formed by the intersection of the cam tangent line and the central axis is the cam angle. In the clamp jaw actuation mechanism illustrated in FIG. 11, the cam tangent line is a line parallel to a line running through slot 54 which is tangential to distal most point 68 of first interior camming surface 64. Thus, in the embodiment of FIG. 11, the angle 67 formed by the intersection of the cam tangent line and the central axis is the cam angle. For the purposes of the present invention, the camming angle is generally greater than 20 degrees.

It will be apparent that an actuation mechanism according to the present invention may be used with any number of surgical instruments, and, in particular, in any surgical instrument where an actuation rod is used to drive one or more elements of an end effector. Such surgical instruments may include, for example; scissors, graspers, forceps, clamps, electrosurgical devices or other devices. It will also be apparent that the present invention may be incorporated into a number of jaw closure arrangements. For example, in certain embodiments of the present invention, alternate elements may be substituted for the actuation rod, in particular, in a device according to the present invention which uses a tube closure mechanism, the moveable tube may be substituted for the actuation rod.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:'

1. A surgical instrument including an actuation mechanism for actuating an end effector at a distal end of said surgical instrument, wherein said actuation mechanism comprises:

a) a camming pivot, wherein said camming pivot comprises:
   i) a lever arm having a first position and a second position
   ii) a first cam at a distal end of said lever arm, said first cam comprising:
      A) a first camming pin;
      B) a first camming slot operatively associated with said first camming pin;
   iii) a second cam positioned distally from said first cam, said second cam comprising:
      A) a second camming pin;
      B) a second camming slot operatively associated with said second camming pin;
b) an actuation rod operatively coupled to said camming pivot and moveable from a first distal postion to a second distal position corresponding to the first and second position.

2. A surgical instrument according to claim 1 wherein said first camming slot is curved.

3. A surgical instrument including a camming pivot, wherein said camming pivot comprises:
a) an actuation mechanism, wherein said actuation mechanism comprises:
   i) a lever arm having a first position and a second position;
   ii) a first cam at a distal end of said lever arm, said first cam comprising:
      A) a first camming pin positioned on said lever arm;
      B) a first camming slot operatively associated with said first camming pin where in said first camming slot is positioned at a cam angle of greater than approximately twenty degrees;
   iii) a second cam positioned distally from said first cam, said second cam comprising:
      A) a second camming pin positioned on said lever arm;
      B) a second camming slot operatively associated with said second camming pin wherein said second camming slot is substantially parallel to a central axis of said surgical instrument;
b) an actuation rod operatively coupled to said actuation mechanism and moveable from a first distal postion to a second distal position corresponding to the first and second positions.

4. A surgical instrument according to claim 3 wherein said first camming slot is curved.

5. An ultrasonic surgical instrument comprising
a) an end effector, wherein said end effector comprises:
   i) an ultrasonic blade;
   ii) a movable clamping element disposed opposite said blade;
b) an actuation mechanism operatively connected to said moveable element, wherein said actuation mechanism comprises:
   i) a lever arm having a first position and a second position;
   ii) a first cam at a distal end of said lever arm, said first cam comprising:
      A) a first camming pin positioned on said lever arm;
      B) a first camming slot operatively associated with said first camming pin where in said first camming slot is positioned at an angle to a central axis of said instrument;
   iii) a second cam positioned distally from said first cam, said second cam comprising:

A) a second camming pin positioned on said lever arm;

B) a second camming slot operatively associated with said second camming pin wherein said second camming slot is substantially parallel to said central axis, c) an actuation rod operatively connected to said lever arm and to said moveable clamping element and moveable from a first distal postion, to a second distal position corresponding to the first and second position.

6. An ultrasonic surgical instrument according to claim 5 wherein said first camming slot is curved.

7. An ultrasonic surgical instrument according to claim 5 wherein said first camming slot is positioned at a camming angle of greater than twenty degrees.

8. A surgical instrument including a camming pivot, wherein said camming pivot comprises:

a) an actuation means for moving an end effector, wherein said actuation means comprises:

i) a lever arm having a first position and a second position;

ii) a: first camming means for translating arcuate motion of said lever arm to linear motion, said first camming means being located at a distal end of said lever arm;

iii) a second camming means for translating arcuate motion of said lever arm to linear motion, wherein said second camming means is positioned distally from said first camming means;

b) a linkage means for coupling said end effector to said actuation mechanism and moveable from a first distal postion to a second distal position corresponding to the first and second position.

9. A surgical instrument according to claim 8 wherein said first camming means comprises a first camming pin movably positioned in a first camming slot.

10. A surgical instrument according to claim 9 wherein said first camming slot is curved.

11. A surgical instrument according to claim 9 wherein said second camming means comprises a second camming pin movably positioned distal to said first camming pin in a second camming slot.

12. A surgical instrument according to claim 11 wherein said first camming slot is positioned at a camming angle of greater than twenty degrees and said second camming slot is substantially parallel to a central axis of said surgical instrument.

13. A surgical instrument including an actuation mechanism for use in surgical instruments, wherein said actuation mechanism comprises:

a) a camming pivot means for translating arcuate motion into linear motion, wherein said camming pivot means comprises:

i) a lever arm having a first position and a second position ii) a first camming means for translating a first portion of said arcuate motion into a first portion of said linear motion, said first camming means being located at a distal end of said lever arm, said first camming means comprising:

A) a first camming pin;

B) a first camming slot operatively associated with said first camming pin;

iii) a second camming means for translating a second portion of said arcuate motion into a second portion of said linear motion, wherein said second camming means is positioned distally from said first camming means, said second camming means comprising:

A) a second camming pin;

B) a second camming slot operatively associated with said second camming pin;

b) an actuation means for transmitting force from said camming pivot means to an end effector and moveable from a first distal postion to a second distal positions corresponding to the first and second position.

14. A surgical instrument according to claim 13 wherein said first camming slot is curved.

15. A surgical instrument according to claim 13 wherein said first camming slot is positioned at a camming angle of greater than twenty degrees and said second camming slot is substantially parallel to said actuation rod.

\* \* \* \* \*